United States Patent
Harrison et al.

(10) Patent No.: US 7,093,594 B2
(45) Date of Patent: Aug. 22, 2006

(54) DOSING DEVICE

(75) Inventors: Nigel Harrison, Linton (GB); Daniel Godfrey, Cambridge (GB)

(73) Assignee: Pfizer Limited, Sandwich (GB)

( * ) Notice: Subject to any disclaimer, the term of this patent is extended or adjusted under 35 U.S.C. 154(b) by 102 days.

(21) Appl. No.: 10/398,066

(22) PCT Filed: Sep. 24, 2001

(86) PCT No.: PCT/GB01/04249

§ 371 (c)(1),
(2), (4) Date: Sep. 12, 2003

(87) PCT Pub. No.: WO02/26301

PCT Pub. Date: Apr. 4, 2002

(65) Prior Publication Data

US 2004/0025870 A1    Feb. 12, 2004

(30) Foreign Application Priority Data

Sep. 29, 2000  (GB) ................................. 0023845.1
Nov. 22, 2000  (GB) ................................. 0028444.8

(51) Int. Cl.
*A61M 15/00* (2006.01)

(52) U.S. Cl. ........................... 128/203.15; 128/203.12; 128/200.14

(58) Field of Classification Search ........... 128/203.12, 128/200.12, 200.25, 203.14, 203.15, 203.21, 128/200.22, 200.23, 203.26, 200.14; D24/110
See application file for complete search history.

(56) References Cited

U.S. PATENT DOCUMENTS

| | | | | |
|---|---|---|---|---|
| 3,826,413 A | * | 7/1974 | Warren | .................. 222/402.13 |
| 4,664,107 A | * | 5/1987 | Wass | ...................... 128/200.23 |
| 4,955,371 A | | 9/1990 | Zamba et al. | |
| 5,027,808 A | * | 7/1991 | Rich et al. | ............. 128/203.23 |
| 5,031,610 A | | 7/1991 | Armstrong et al. | |
| 5,060,643 A | * | 10/1991 | Rich et al. | ............. 128/200.23 |
| 5,069,204 A | * | 12/1991 | Smith et al. | ........... 128/200.23 |
| 5,119,806 A | * | 6/1992 | Palson et al. | .......... 128/200.14 |

(Continued)

FOREIGN PATENT DOCUMENTS

EP    0 045 419 A1    2/1982

(Continued)

OTHER PUBLICATIONS

International Application Published under the Patent Cooperation Treaty (PCT), Publication No. WO 93/24167, Publication Date: Dec. 9, 1993, Inventors: Holroyd et al., 23 pages.

(Continued)

*Primary Examiner*—Henry Bennett
*Assistant Examiner*—Dinnatia Doster-Greene
(74) *Attorney, Agent, or Firm*—Reising, Ethington, Barnes, Kisselle, P.C.

(57) ABSTRACT

A dosing device comprising a dispenser (26) for dispensing a dose material and a dose actuation mechanism (44) is provided. The dose actuation mechanism (44) comprises a number of integrally hinged links (52, 54, 55) which are connected to each other at hinging points. A deflectable tongue (157), moveable in response to air flow from inhalation by a patient is attached to a first link (52), to move the first link in response to air flow, movement of the first link being transferred to a second link (54) to cause actuation of the dispenser. The first link rests at an over center, or stable, position prior to operation, and moves under center during operation of the device to trigger movement of the second link. The dose actuation mechanism is a one-piece moulding from plastics material.

25 Claims, 12 Drawing Sheets

U.S. PATENT DOCUMENTS

| | | | |
|---|---|---|---|
| 5,133,343 A | | 7/1992 | Johnson, IV et al. |
| 5,184,761 A | | 2/1993 | Lee |
| 5,217,004 A | * | 6/1993 | Blasnik et al. ......... 128/200.23 |
| 5,224,472 A | | 7/1993 | Pesenti et al. |
| 5,349,945 A | * | 9/1994 | Wass et al. ............ 128/200.23 |
| 5,408,994 A | * | 4/1995 | Wass et al. ............ 128/203.15 |
| 5,447,150 A | | 9/1995 | Bacon |
| 5,507,281 A | | 4/1996 | Kuhnel et al. |
| 5,511,540 A | | 4/1996 | Bryant et al. |
| 5,546,932 A | * | 8/1996 | Galli ..................... 128/203.15 |
| 5,772,085 A | | 6/1998 | Bryant et al. |
| 5,826,571 A | * | 10/1998 | Casper et al. ......... 128/200.23 |
| 6,026,808 A | | 2/2000 | Armer et al. |
| 6,029,662 A | | 2/2000 | Marcon |
| 6,095,141 A | | 8/2000 | Armer et al. |
| 6,142,339 A | * | 11/2000 | Blacker et al. ............... 222/23 |
| 6,357,442 B1 | | 3/2002 | Casper et al. |
| 6,755,190 B1 | * | 6/2004 | Rasmussen ............ 128/200.23 |

FOREIGN PATENT DOCUMENTS

| | | |
|---|---|---|
| EP | 0 414 536 A2 | 2/1991 |
| EP | 0 490 797 A1 | 6/1992 |
| EP | 1 008 360 A1 | 6/2000 |
| EP | 1 008 361 A2 | 6/2000 |

OTHER PUBLICATIONS

International Application Published under the Patent Cooperation Treaty (PCT), Publication No. WO 98/52634, Publication Date: Nov. 26, 1998, Inventors: MacMichael et al, 35 pages.

International Application Published under the Patent Cooperation Treaty (PCT), Publication No. WO 98/56444, Publication Date: Dec. 17, 1998, Inventors: Rand et al., 33 pages.

International Application Published under the Patent Cooperation Treaty (PCT), Publication No. WO 98/56445, Publication Date: Dec. 17, 1998, Inventors: Rand et al., 28 pages.

International Application Published under the Patent Cooperation Treaty (PCT), Publication No. WO 99/49916, Publication Date: Oct. 7, 1999, Inventors: Andersson et al., 31 pages.

International Application Published under the Patent Cooperation Treaty (PCT), Publication No. WO 99/65551, Publication Date: Dec. 23, 1999, Inventors: Sosiak et al., 40 pages.

International Application Published under the Patent Cooperation Treaty (PCT), Publication No. WO 00/16835, Publication Date: Mar. 30, 2000, Inventors: Christrup et al., 30 pages.

International Application Published under the Patent Cooperation Treaty (PCT), Publication No. WO 00/16836, Publication Date: Mar. 30, 2000, Inventors: Christrup et al., 27 pages.

International Application Published under the Patent Cooperation Treaty (PCT), Publication No. WO 00/16837, Publication Date: Mar. 30, 2000, Inventors: Christrup et al., 26 pages.

International Application Published under the Patent Cooperation Treaty (PCT), Publication No. WO 00/16838, Publication Date: Mar. 30, 2000, Inventors: Christrup et al., 30 pages.

International Application Published under the Patent Cooperation Treaty (PCT), Publication No. WO 00/29054, Publication Date: May 25, 2000, Inventors: Bryant et al., 23 pages.

* cited by examiner

DOSING DEVICE

FIELD OF INVENTION

This invention concerns a dosing device for drug delivery and in particular relates to devices such as inhalers and injectors, and a mechanism for use in such devices.

BACKGROUND TO THE INVENTION

In treatment for asthma and other respiratory problems, a dosing device such as an inhaler can be used to produce an aerosol mist or cloud of fine particles for inhalation into a patient's lungs. Typically inhalers are either manually-operated or breath-operated. Breath-operated inhalers have certain advantages in that the dose given is necessarily in synchronism with intake of breath by the patient, whereas manually operated devices require a patient to breathe in as a button is pressed, sometimes resulting in ineffective dosing due to the intake of breath being wrongly timed.

Breath-operated inhalers are known, for example U.S. Pat. No. 3,565,070 and WO98/52634. These inhalers are known as metered-dose inhalers (MDI's) and consist of a small canister containing medication with a metering valve and a valve stem. The MDI delivers a metered dose to the patient when the valve stem is depressed. However a large force is required to depress the valve stem and so release the dose, and a problem in the design of breath-operated MDI's is how to achieve release of such a large force using only a very small force available from the patient's breath. This problem is partly overcome by using a large spring to a sufficient force to actuate the device. The spring is compressed by the patient, either by a positive "cocking" process or automatically when the patient opens the mouthpiece cover. The energy stored in the spring is then released by a trigger operated by the patient's breath.

Components forming the trigger are limited in size by the dimensions of the MDI, which is a hand-held device. The trigger also needs to be able to open the valve reliably only when a dose is required and for the life of the device.

MDI's are beginning to use hydrofluroroalkanes (HFA's) as aerosol propellants within the canister. The HFA's need to be held at a pressure of around 5–6 bar, and certain valves can require forces of up to 50N for operation. This further increases the difficulties in achieving a trigger which can operate consistently and reliably.

The present invention aims to provide an inhaler with a dose actuation mechanism which consistently results in delivery of a dose from an inhaler in response to a patient's breath.

SUMMARY OF THE INVENTION

In accordance with one aspect of the present invention, there is provided a dosing device comprising a dispenser for dispensing a dose material and a dose actuation mechanism comprising a first link and a second link, wherein the second link comprises a first element and a second element hinged together at a hinging point, and a first end of the first link attached to, or permanently adjoining, the second link near the hinging point, such that the first link is moveable in response to air flow and its movement is transferred to the second link to cause actuation of the dispenser.

The first link is thus responsive to a small force produced by a patient inhaling, so as to move the second link and release a further force to actuate the dispenser. In this way operation of an inhaler using a breath can be achieved.

The first link may comprise third and fourth elements hinged together at a second hinging point, with the second hinging point arranged to abut a stop so as to ensure that the first link is held in an over center position when in the rest position prior to operation of the device. Preferably a deflectable member is attached to the third element and is moveable in response to air flow, so as to cause the first link to move. The deflectable member is typically a vane, tongue or air flap.

Where the first link rests at an over center, or stable, position prior to operation, the first link moves under center during operation of the device to trigger movement of the second link.

The hinged elements are independently moveable about the respective hinging points and for the first link, in the rest position, the third and fourth elements are preferably disposed about the second hinging point to form a V-shape, with a force acting on the second hinging point to maintain the V-shaped link in an over center position. The force may be provided by an abutment.

The second link is preferably arranged so that it is held in an under center position by the first link and is moveable to further under center in response to movement of the first link. Again this is typically achieved by the first and second elements being disposed about the first hinging point so as to form a substantially V-shape.

The dose actuation mechanism may further comprise a third link comprising fifth and sixth elements joined at a third hinging point, one end of the second link connected to or permanently adjoining near the third hinging point.

Thus the dose actuation mechanism comprises a number of integrally hinged links connected to each other at hinging points separate from integral hinges of each link.

Alternatively the dose actuation mechanism may comprise a fourth link comprising seventh and eighth elements joined at a fourth hinging point, a second end of the first link connected to the fourth link, near or permanently adjoining, the fourth hinging point, such that the first link is interposed between the second and fourth links.

A biasing means, such as a spring, may adjoin the second hinging point. This configuration allows the second link to be substantially straight along its length, the first and second elements forming a substantially planar link. In this arrangement, the third link may also be arranged to be substantially straight, the biasing means urging against the second hinging point so as to ensure that the substantially straight second link responds to movement of the first link to transfer force along the mechanism.

The mechanism may be thought of as using a stable over center link to trigger at least one under center link. By connecting a plurality of under center links in series, the first over center link can be used to trigger a series of individual links in succession, so as to amplify a mechanical advantage along the chain of collapsing links.

The first link is preferably maintained so that the third and fourth elements subtend as maximum an arc about the second hinging point as possible, i.e. so as to form a substantially linear link, so that a small force is needed to actuate the first link. This ensures that the small force generated by inhalation acting on a vane or other such member can result in movement of the first link.

Whilst the invention has been described with reference to two, and/or three links, it is to be understood that the invention can be extended to a succession of links, i.e. to a number N of links where the number N is only limited by the size of the device in which the mechanism is to be placed.

The links successive to the first link are held in their primed position by the preceding links, with the first link moving from a primed position to a fired position to cause subsequent links in turn to move from a primed position to a fired position.

Preferably the first and second links, or first, second and third links, or N links are formed in a one-piece moulding made from plastics material, polypropylene or nylon.

The invention also lies in a dose actuating mechanism as aforesaid, and in such a mechanism made as a one-piece moulding from plastics material.

BRIEF DESCRIPTION OF THE DRAWINGS

The invention will now be described by way of example, and with reference to the accompanying drawings, in which.

DETAILED DESCRIPTION OF THE PREFERRED EMBODIMENT

Figure 1:
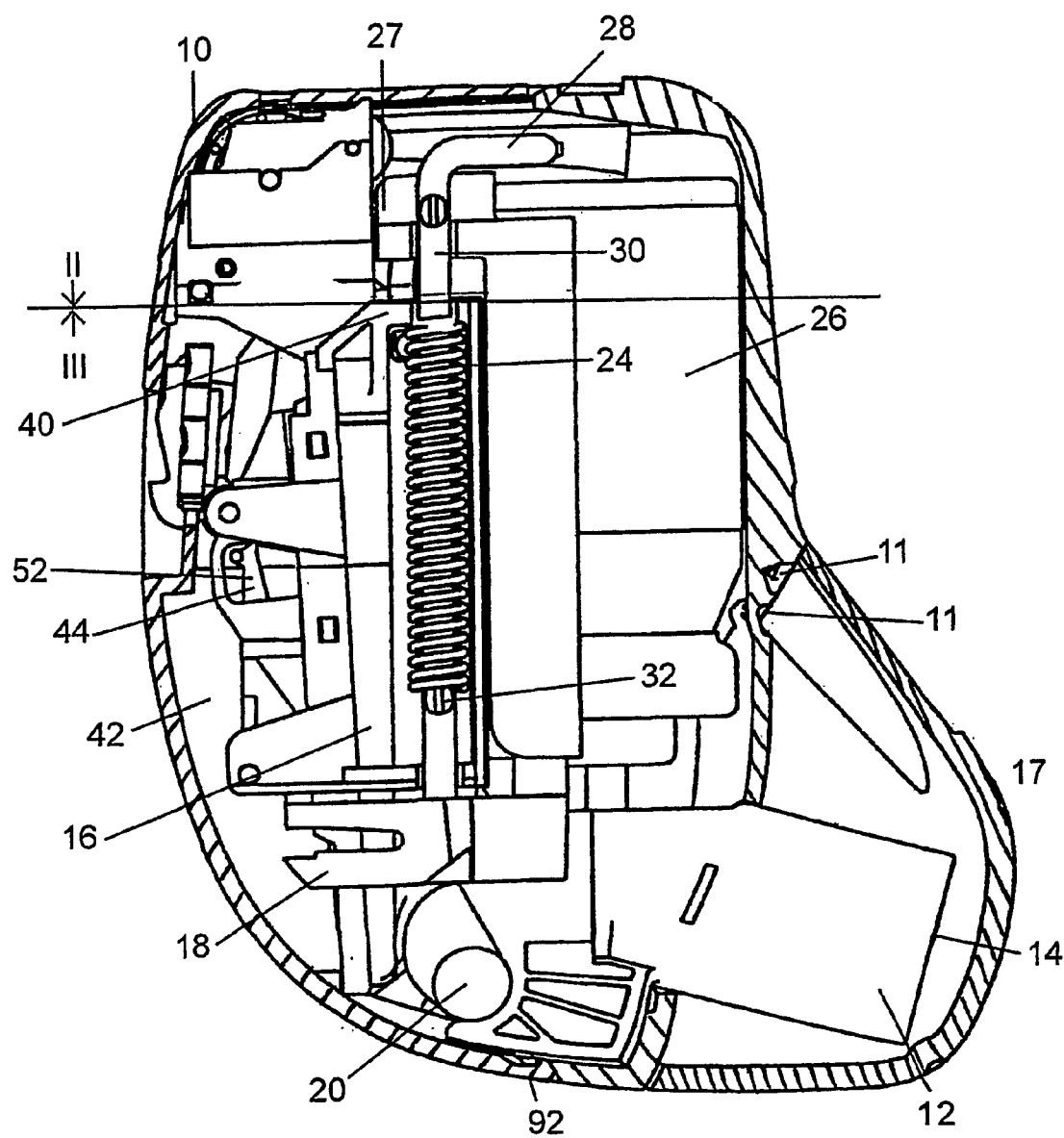
FIG. 1 is a partial sectional view through an inhaler in accordance with the present invention illustrating a first embodiment of a dose actuation mechanism.
Figure 8:
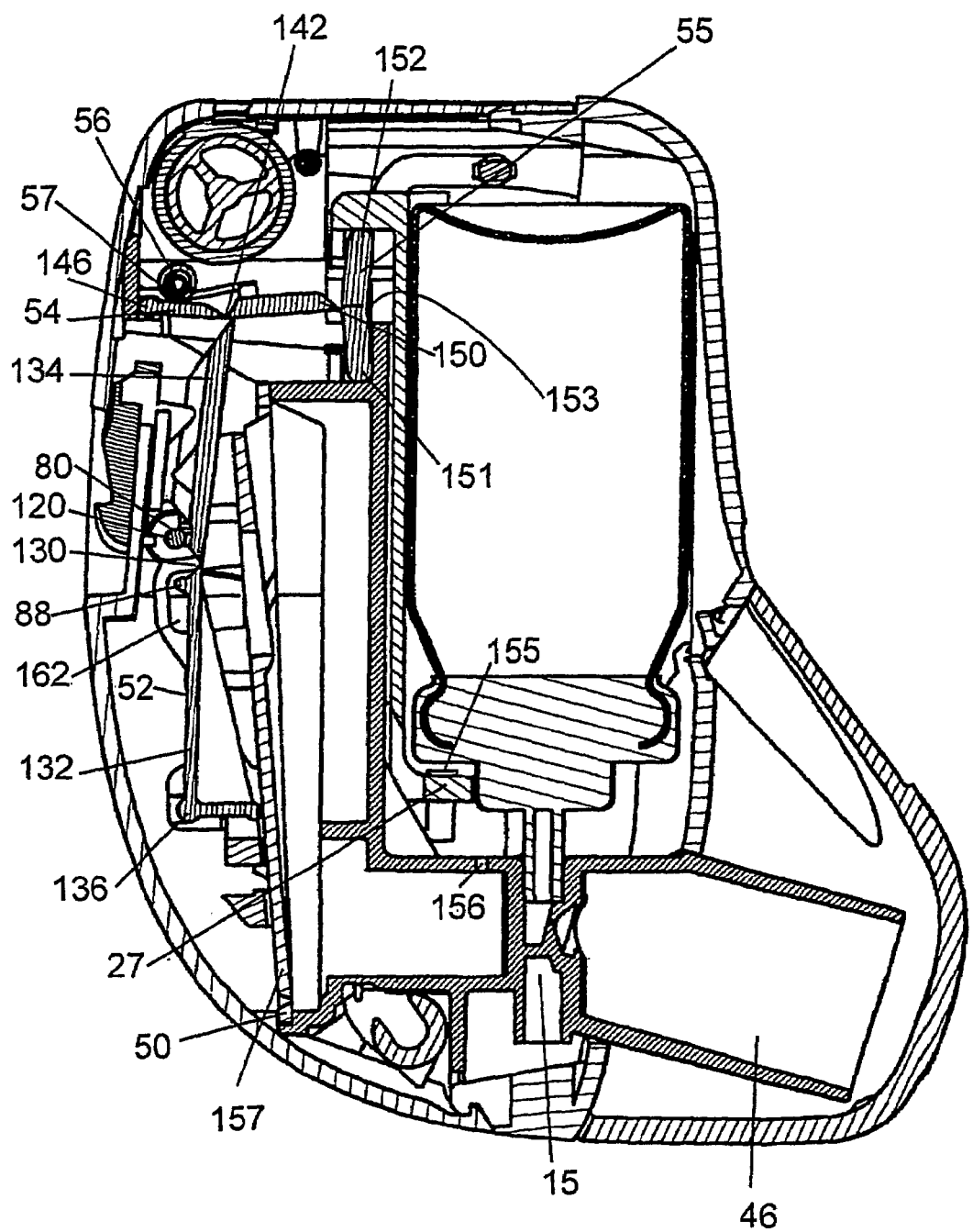
FIG. 8 is a vertical section along the line VI—VI of FIG. 4 illustrating the dose-actuation mechanism before firing to dispense a dose.

FIGS. 1 and 8 show a breath-operated metered dose inhaler (MDI) in accordance with the present invention which comprises a hollow outer body 10 typically made of plastics material, which includes a mouthpiece moulding 12 comprising a mouthpiece 14, stem block 15 and chassis 16. A cover 17 for the mouthpiece, which incorporates a central aperture, is attached to the body by a cam 20 which pivots as the cover 17 is moved. When the cover is closed, the cam 20 rotates and pushes upwards against a cam saddle 18 which compresses main springs 24 and stores energy in the springs for later release. The cam bears the full force of the main springs 24. In this cover closed condition, the inhaler is in a rest position awaiting firing to deliver a dose of medication from a dispenser in the form of a canister 26 cradled in a canister carriage 27 contained within body 10. The medication is suspended in a propellant of the hydrofluoroalkane type (HFA's).

The canister 26 is positioned within the body 10 between a canister carriage 27 and a steel bar or hook 28 forming part of a substantially u-shaped spring carriage 30 bearing the two main springs 24 disposed on either side of the canister 26. In this rest position of the inhaler, the canister is relatively loose and is only held in place because a valve stem 31 of the canister is held within the stem block 15. The canister 26 is thus only secured by the valve stem 31, with a canister valve spring in the valve stem 31 and the lack of force on the canister ensuring that the valve 31 does not leak.

Part way along the spring carriage 30, a swaged abutment 32 holds main springs 24 against a support 40 moulded into the chassis. The main springs are shown in FIG. 1 in a compressed state, storing energy, with the strength of the main springs 24 chosen to apply a force of around 40–60N to ensure that the valve stem 31 operates reliably.

The body 10 defines a holding area 42 in which a dose-actuation mechanism 44 is situated and also an air passage 46 in which a vane element 50 is located. The vane element comprises an outer frame bearing a membrane on which a tongue is carried, the tongue deflecting in response to small changes in pressure. The trigger mechanism 44 which is 7 mm deep, i.e. extends into FIG. 1 for a distance of 7 mm, comprises a trigger link 52, an intermediate link 54 and a power link 55 and is typically made as a one-piece moulding from polypropylene. A biasing torsion spring 56 is held on a roll pin 57 supported in the chassis, the biasing torsion spring 56 being held in compression between the chassis and a mounting position 154 on the uppermost surface of the intermediate link 54, which is in turn supported by the trigger link.

Figure 2:
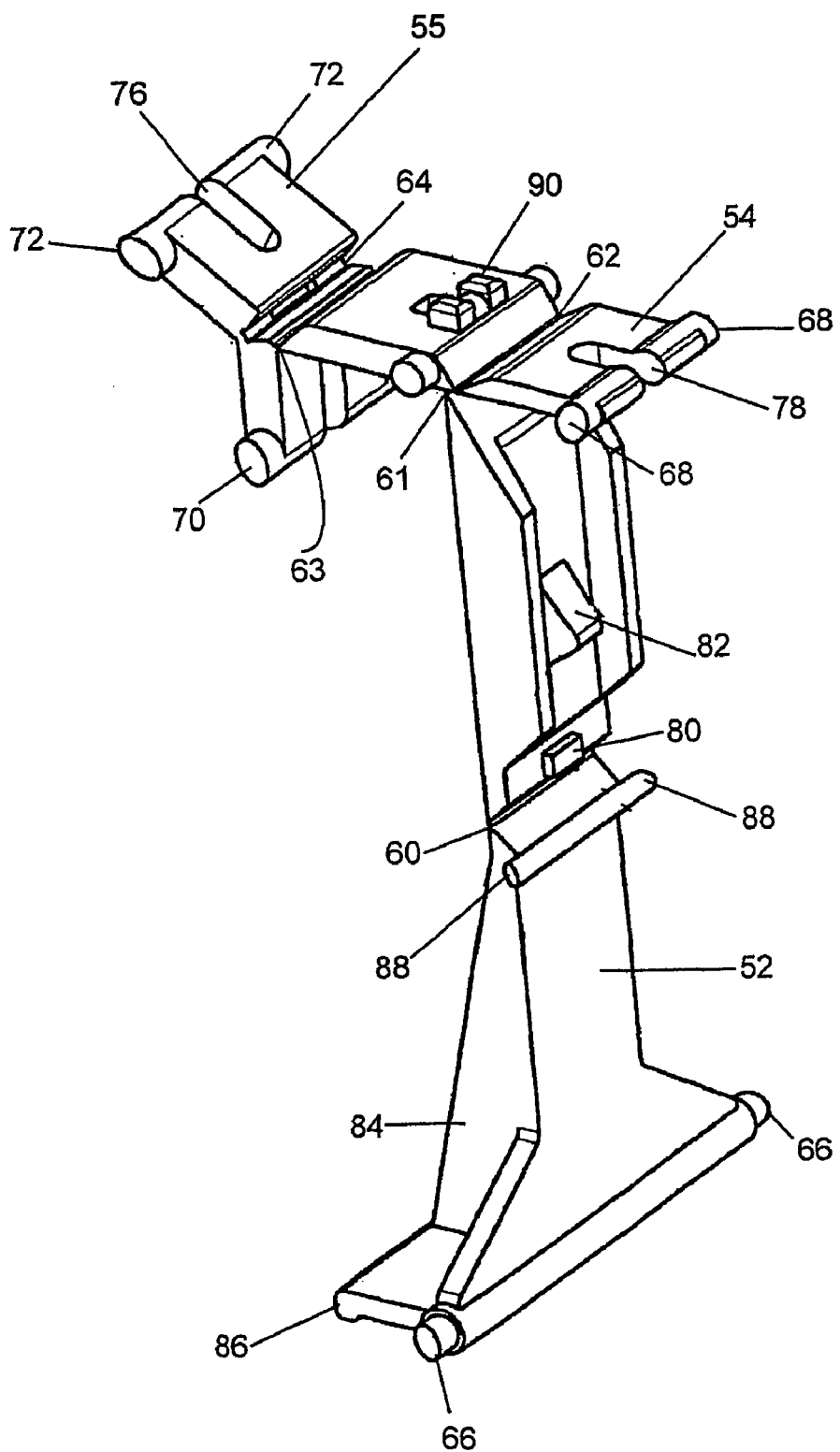
FIG. 2 is a perspective view of the first embodiment of the dose actuation mechanism.
Figure 3:
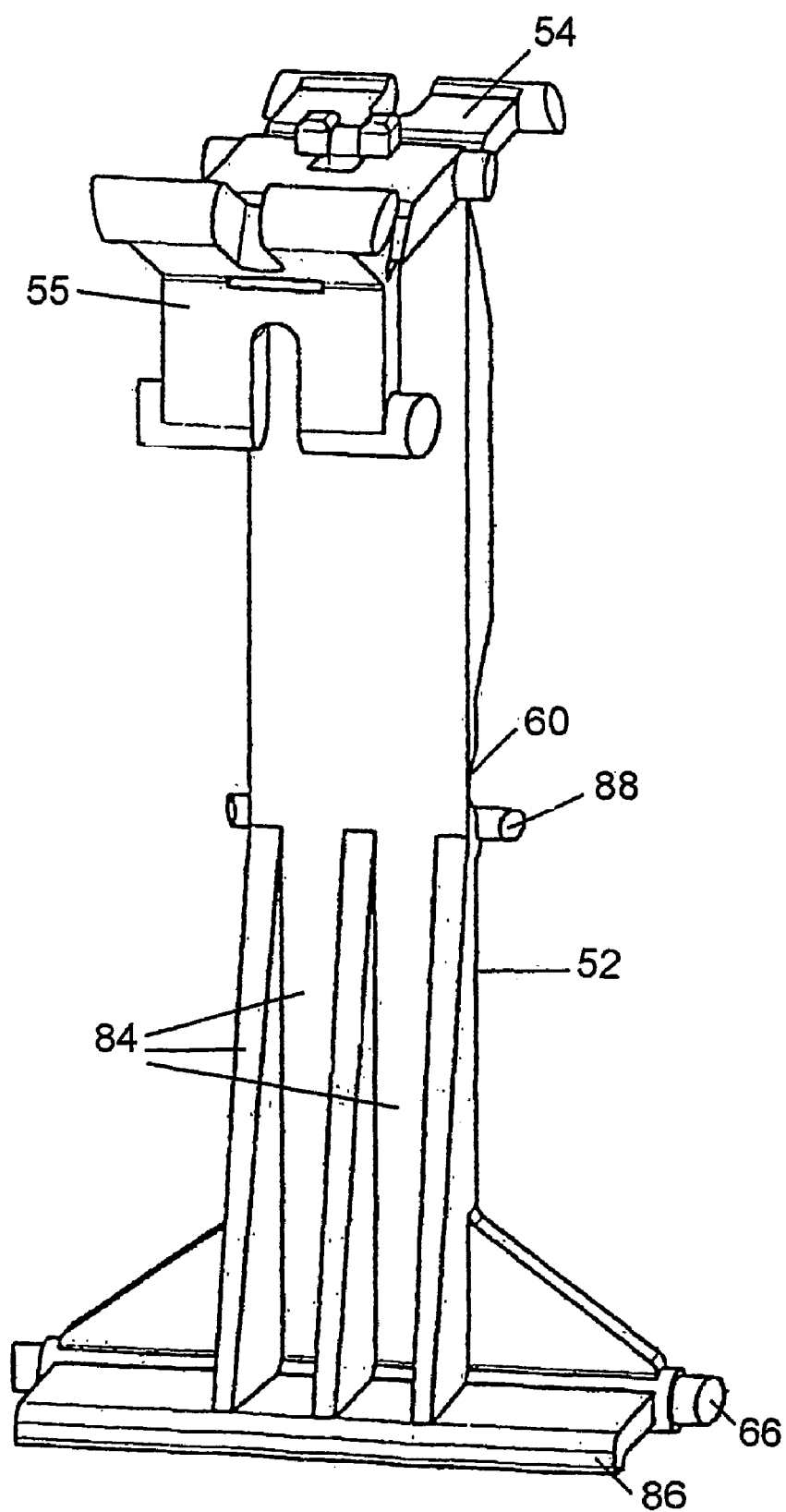
FIG. 3 is a view from one side of the dose actuation mechanism shown in FIG. 2.

The three main elements of the dose actuation mechanism, namely the trigger link 52, the intermediate link 54 and the power link 55 can be clearly seen in FIGS. 2 and 3. The trigger link 52 is generally of thickness of around 1 mm in section and tapers to a central hinging point 60 which is around 100 microns thick. An upper end of the trigger link hinges to the intermediate link at hinging point 61 which is close to a central hinging point 62 of the intermediate link 54. Similarly the end of the intermediate link closest to the power link hinges to the power link at the hinging point 63 which is close to a centre hinging point 64 of the power link. Each link is thus formed from two hinged elements with one element of the trigger link being hinged to the intermediate link and one element of the intermediate link being hinged to the power link. The links are of similar cross-section, with the intermediate link being around 1 mm thick and the power link being 2 mm thick.

The central hinge 64 of power link 55 is formed by a pair of hinge straps 0.5 mm thick between the two elements forming the power link. The top and bottom ends of the power link and the free end of the intermediate link contain central slots 76, 78 which allow the links to be temporarily squeezed together for insertion into the chassis. Pins 66, 68, 70 and 72 locate in the chassis to secure the one-piece moulding of the trigger mechanism in position within the body of the device. A lug 80 is provided on an upper part of the trigger link and this lug contacts a backstop pin 120 positioned in the chassis to set the over center distance of the two elements of the trigger link. A triangular upstanding section 82, also on the upper part of the trigger link, provides a lug on which a manual override button acts to actuate the trigger mechanism if required.

Strengthening ribs 84 are provided on the rear of the lower section of the trigger link, as can be seen more clearly in FIG. 3, and at the bottom of the trigger link, there is provided a lever arm 86 which is pushed to reset the trigger mechanism. Pins 88 carried on the lower part of the trigger mechanism near the central hinge locate in apertures on the vane element so that movement of the tongue causes deflection of the trigger element. The intermediate link 54 carries a saddle and recess pair 90 which is driven by the end of biasing torsion spring 56.

Figure 4:
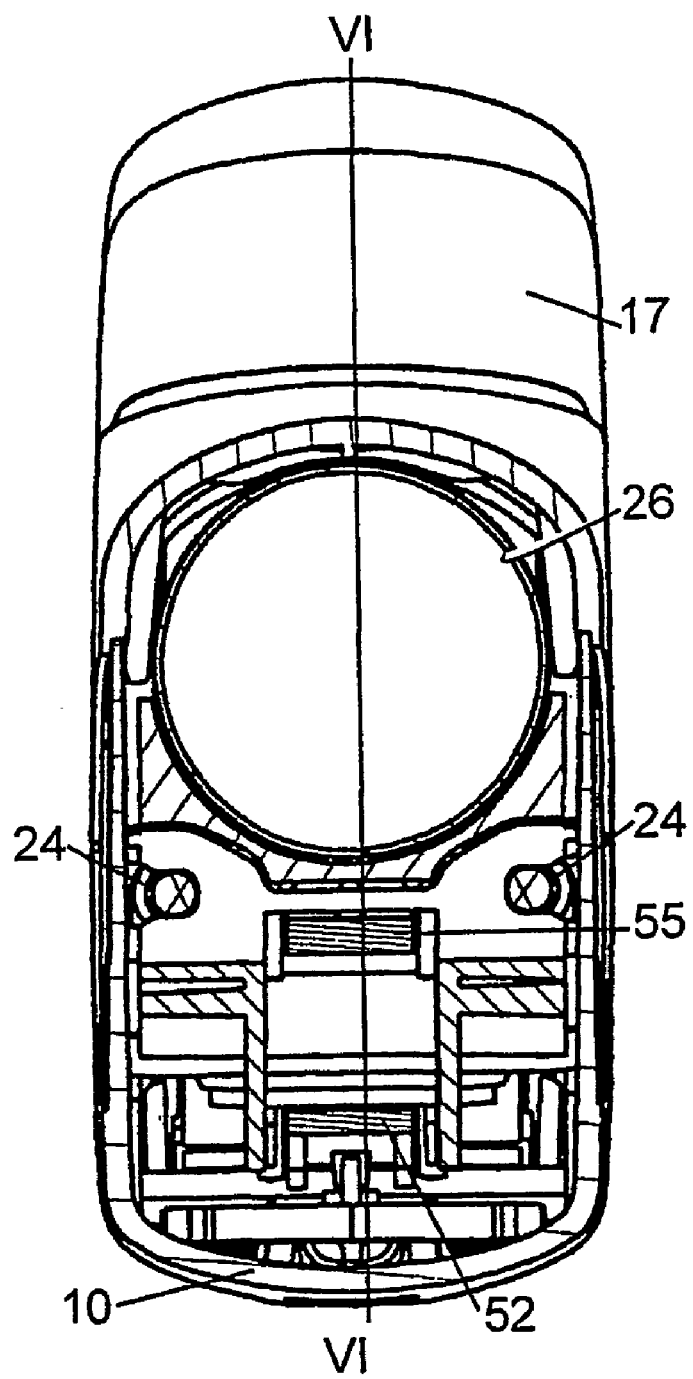
FIG. 4 is a sectional view across the line II—II of FIG. 1 when looking downwards.
Figure 5:
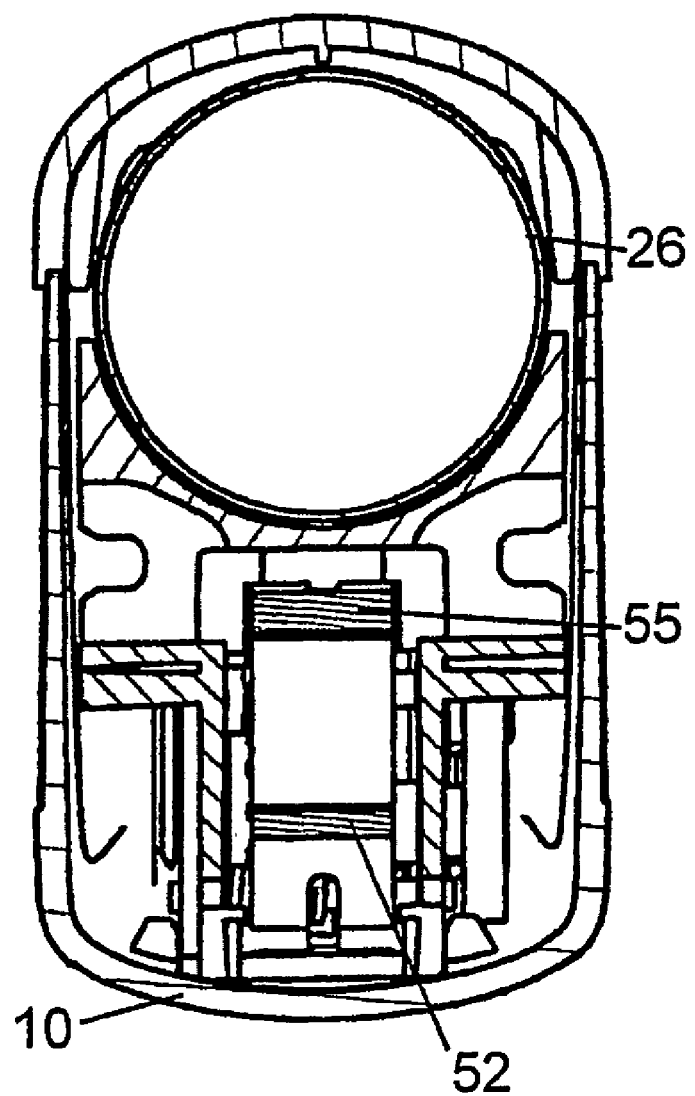
FIG. 5 is a sectional view across the line III—III of FIG. 1 when looking towards the top of the inhaler.

FIG. 4 shows a section through the inhaler across line II—II of FIG. 1, looking down towards a base 92 of the inhaler. Common reference numerals to those used in FIG. 1 have been used where appropriate, and it can be seen that a power link 55 and trigger link 52 are substantially rectangular in cross-section. An equivalent section is shown in FIG. 3 but looking away from the base 92 of the inhaler.

In FIG. 1, the device is shown in the cover closed, or rest, condition before delivery of a dose to the patient. Operation of the device will be described later with reference to the FIGS. 8 to 10 but operation of the links forming the dose-actuation mechanism 44 will now be discussed with reference to FIGS. 6 and 7.

Figure 6:
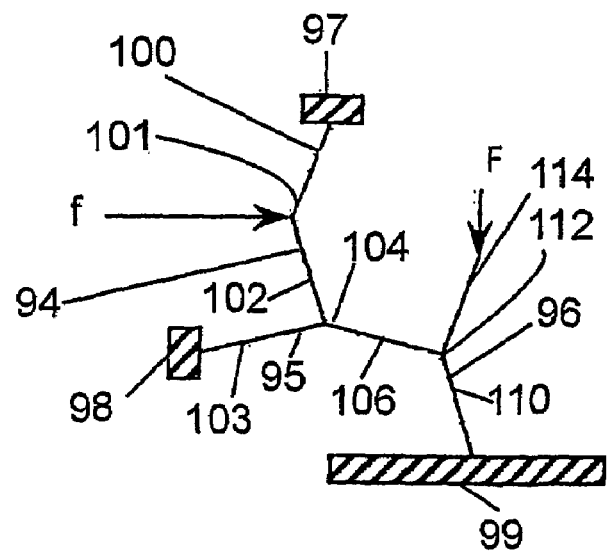
FIG. 6 is a schematic diagram used to explain operation of a first embodiment of a dose actuation mechanism in accordance with the invention.

One embodiment of the dose-actuation mechanism is shown schematically in FIG. 6. This mechanism is similar to that shown in FIGS. 1 and 7 and comprises a trigger link 94, an intermediate link 95 and a power link 96 which are held in position by fixed stages 97, 98, 99, a small force f and a large force F. Each collapsing link comprises first and second elongate elements which are hinged together. The trigger link 94 thus comprises a first elongate element 100 connected by hinge 101 to a second elongate element 102. The intermediate link comprises a third elongate element 103 connected by hinge 104 to a fourth elongate element 106, with the power link 96 comprising a fifth elongate element 110 connected by hinge 112 to sixth elongate element 114.

The first element 100 is pivotally affixed to stage 97, with the second element 102 permanently pivotally affixed close to the hinging point 104 of the intermediate link 95. The intermediate link 95 is pivotally attached at one end to stage 98 with the other end of the link being permanently pivotally affixed close to the hinging point 112 of the power link 96. The fifth element 110 of the power link is pivotally affixed at one end to a third stage 99, with one end of the sixth element 114 bearing the highest load of all the elements, this being around 40N or 60N, i.e. the force associated with the main spring. A small force is incident close to the hinge 101 of the trigger link 94, and is provided by pin 120 as shown in FIG. 8.

Each link is therefore attached at one end to a fixed pivot point and attached to the preceding link at its hinging point, such that movement of one link on the chain results in movement of the next link in the chain.

The trigger mechanism in FIG. 6 is shown in equilibrium, the links being stable and supporting the force F associated with the main biasing spring. The trigger link 94 is in a stable or over center position due to the small force f, whilst the intermediate link 95 and the power link 96 are both in an unstable, or under center, position.

With over center position, force acting in the same direction as the intended collapse movement of the link is required to keep the link in equilibrium. With an under center position, a force needs to act in the opposite direction to the intended collapse direction to keep the link in equilibrium. Thus an over center position is where without an additional counteracting force, a link would move through a centre line of unstable equilibrium and beyond whereas an under center link would move away from, and not pass through, the centre line of unstable equilibrium.

The degree of over and under center has been exaggerated in FIG. 6 for the sake of clarity. In the interests of stability, any over center link must be over center by a significant amount. However this limits the mechanical amplification that can be achieved for any individual link as the best ratio of forces is achieved for a link close to straight.

When a collapsing link is close to straight, i.e. the two hinged elements subtend an arc of nearly 180° about the hinging point, only a small horizontal force is required to maintain equilibrium with a large vertical force. As the link collapses, the ratio between the vertical force and the horizontal force changes such that the horizontal force rises relative to the vertical force. As an example when the links are at 45°, the horizontal force is approximately double the vertical force. Beyond this when the links are almost fully collapsed, the horizontal force is very much larger than the vertical force.

Thus the mechanism can be maintained in equilibrium by force f acting on the trigger link, but yet have the potential to produce a multiplying mechanical advantage along the links as successive links move. When the trigger link 94 in over center position is pushed to an under center position, such as is typically achieved by use of a vane or other air-responsive element attached to the trigger link, the intermediate link 95 moves yet further under center, so causing the power link 96 to move to further under center. The power link thus partially collapses, so that its vertical extent is reduced and it no longer opposes the large force F. In this way, applying a small force to push the trigger link under center results in the large force F being released to actuate dispensing of a dose from the canister.

The power link and the intermediate links can be set very close to straight and hence very high force amplification can be achieved with this type of mechanism. With very high amplification, it is possible to use the triggering link as the flap that moves in response to airflow and hence dispense with the need for additional flap and associated linkage to the trigger link.

As shown here, the embodiment consists of one trigger link, one power link and one intermediate link. However other variations of this embodiment are possible, such as having one trigger link together with one or more power links, and either zero or any number of intermediate links.

Figure 7:
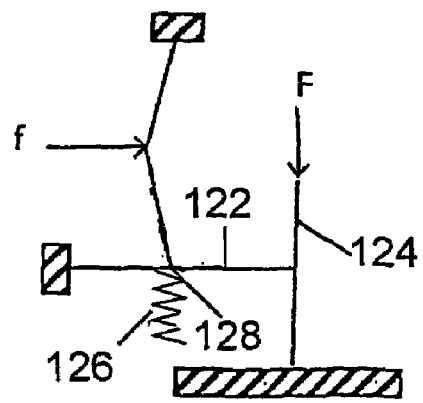
FIG. 7 is a schematic diagram of a third embodiment of a dose-actuation mechanism.

FIG. 7 shows another embodiment of an under center chain as shown in FIG. 4 where an intermediate link 122 and a power link 124 are set straight, and thus in an unstable position, with a biasing spring 126 positioned under a hinging point 128 of the intermediate link 122. Without the biasing spring, movement of the trigger link would not result in any movement of the intermediate link. However as a result of the biasing spring, the trigger link carries a compressive load and once the trigger link starts to move under center, the biasing spring pushes against the intermediate link to make it move under center, which then pulls the power link under center. Force is thus amplified along the mechanism as the links collapse.

Variants on these under center linkages are possible, for example the trigger link can be over center, the intermediate link straight and the power link under center, or the trigger link over center, the intermediate link under center and the power link straight. Thus for all embodiments, the trigger link should be over center to achieve stability.

Figure 9:
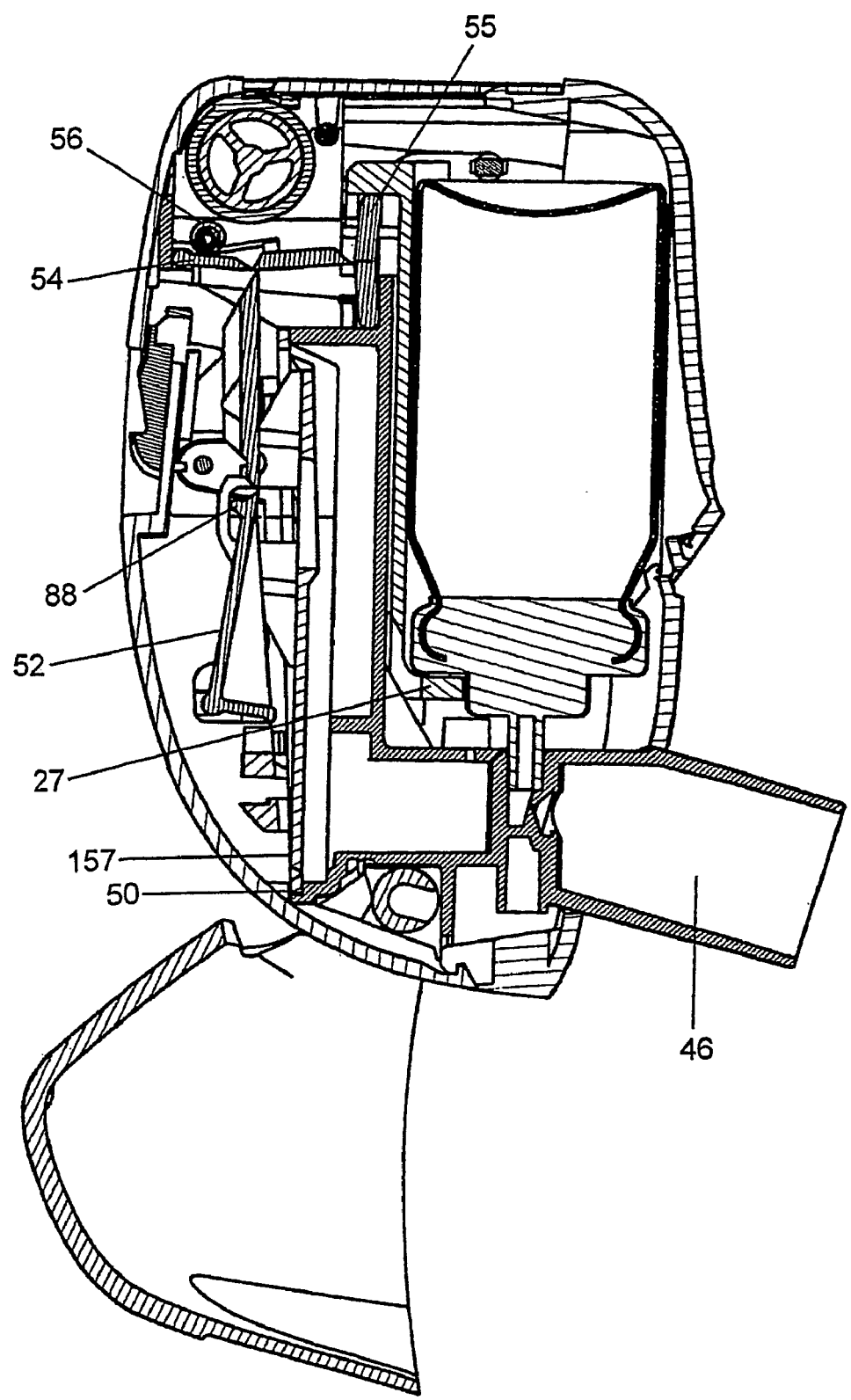
FIG. 9 is a vertical section along the line VI—VI showing movement of the dose-actuation mechanism during mid-fire.

Operation of the inhaler shown in FIG. 1 will now be explained with reference to FIGS. 8 to 10, in which common reference numerals have been used where appropriate.

FIG. 8 illustrates the triggering mechanism 44 in the rest position, with the cover of the inhaler closed and the device ready to dispense a dose. The trigger link 52 is held by biasing torsion spring 56 in a stable over center position with lug 80 resting on pin 120. The trigger link is in a substantially vertical configuration, with a first element 132 and a second element 134 subtending nearly 180° of arc. The near vertical trigger link 52 holds the intermediate link 54 and power link 55 at unstable under center positions.

Pin joints 136, 146, 151, 152 secure the loose ends of the mechanism within the chassis and provide an equivalent securing point to stages 97, 98, 99 in FIG. 6. The end of the second element 134 furthest from the hinging point 130 is permanently hinged to the intermediate link 54 close to the hinge 142, with end 150 of the intermediate link hinged to the power link close to the centre hinging point 153 of the power link. A leg 154 of the biasing torsion spring sits in a saddle 90 on the intermediate link close to central hinge 142 and allows the intermediate link 54 to be substantially straight, although slightly under center.

When a patient wishes to take a dose of medication, they open cover so as to access the mouthpiece. As the cover is opened, the cam 20 rotates, cam follower or saddle 18 moves downwards and steel bar or hook 28 is moved into engagement with the canister 26. As the spring carriage continues its downward movement, the hook 28 pushes the canister a small distance onto the canister carriage 27 and as the canister stem is received in the mouthpiece moulding, this downwards movement causes the canister valve 31 to be partially compressed. A lug 155 on the bottom of the canister carriage restricts travel of the carriage, and hence compression of the valve, such that no dose is released. In this state, the canister carriage is retained in position by the trigger mechanism which now carries most of the force of the main springs. In this primed position, the patient places their mouth over the mouthpiece 14 so as to create a seal and inhales. Air is drawn in through the apertures 156 in the air passageway wall and through the slots 11, creating a through-flow of air which produces a pressure drop of 0.5 kPa in the device which causes the tongue 157 of the pressure-responsive means 50 to move. As the tongue 157 moves in response to an intake of breath, the pin 88 is pulled by edge of aperture 162 so pulling the hinging point 130 of the trigger link 52 away from pin 120, as shown in FIG. 9 where the trigger mechanism is in mid-fire. If required, a small aperture is placed in the air passage 46 to produce an air valve which allows the device to operate in response to a lower pressure drop and to allow free flow of air as the canister is fired.

Figure 10:
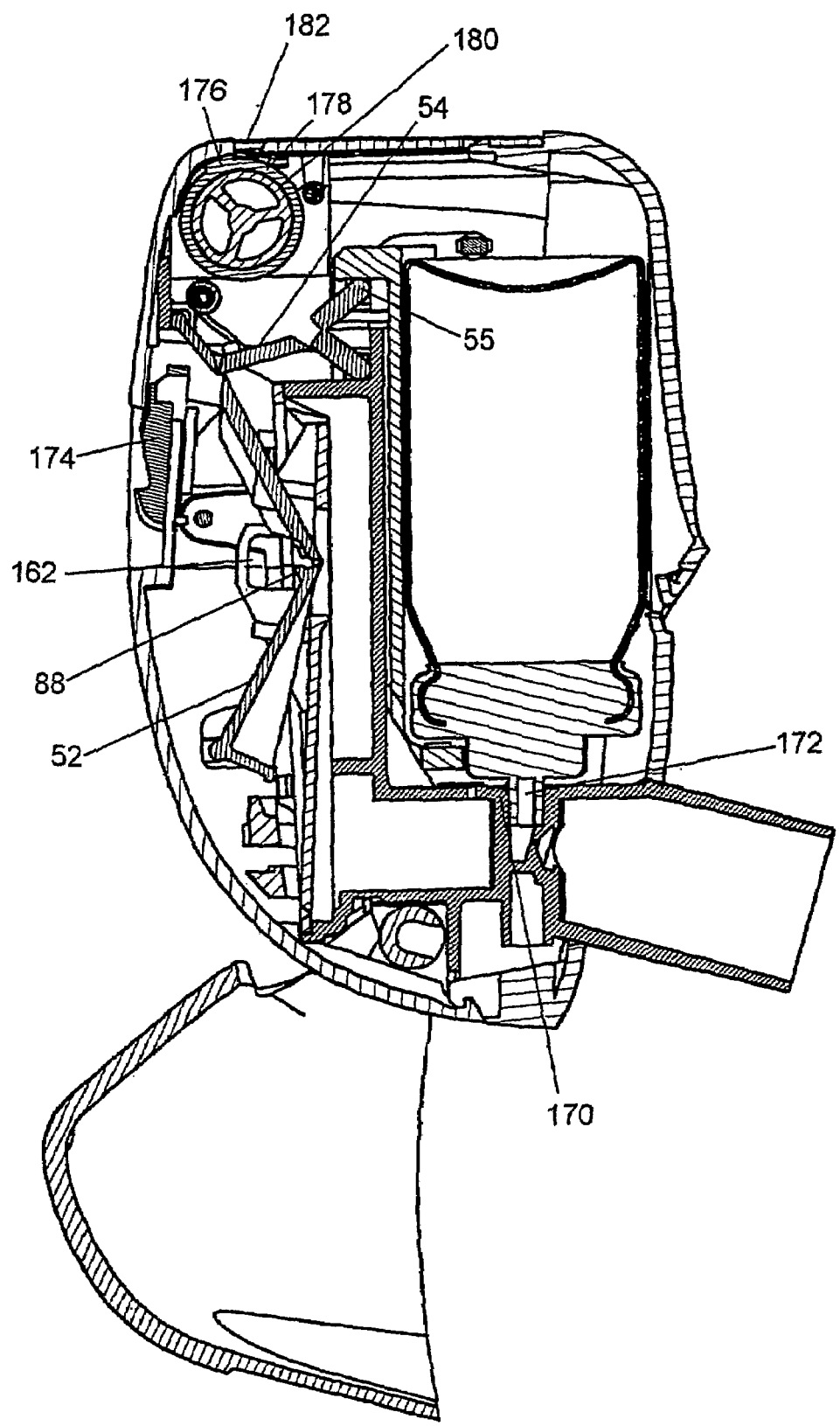
FIG. 10 is a vertical section along line VI—VI of FIG. 4 showing the dose-actuation mechanism after firing.

As the trigger link continues to move, the pin 88 proceeds to the far end of aperture 162, see FIG. 10, and the trigger link 52 moves into an under center position forming a V-shape. As the trigger link 52 moves into this under center position, the biasing torsion spring 56 pushes the intermediate link further under center. The power link 55 is pulled under center due to the interconnection of the power link and the intermediate link, and the power link moves into a substantially V-shape. The overall height of the power link is thus reduced and the main springs 24 are released to expand and urge the canister against stem block 170 and so depress valve stem 172.

This toggle-type trigger mechanism is very sensitive, with only a small pressure drop of around 0.5 kPa across the pressure-responsive means 40 being required to produce a force of around 0.5N to cause the trigger link 54 to move. Once a dose has been dispensed, the cover 16 is closed and the cover cam rotates and pushes against saddle to compress the main springs and to reset the power and trigger links into the rest position. A cantilever carried on saddle 18 pushes the trigger link over center to complete reset of the trigger mechanism.

A sliding manual override button 174 is mounted in case 10 and incorporates a cam that acts on the back of the trigger link so as to push the trigger link under center when the button is slid. The button incorporates return springs to return it to its rest position.

The inhaler includes a dose counter 176 consisting of a rocker, a slotted or geneva wheel, and two drums 178, 180 to represent units and tens digits respectively. The units wheel is numbered zero to nine, with the tens wheel labelled with positions empty, blank, 1 to 12 and this enables the counter to display doses from 129 down to zero to an empty position. The empty position is aligned with a flag moulded onto the tens wheel, with a rectangular aperture 182 in the body 10 allowing to patient to view the number of doses left as shown by the two wheels. In the empty condition, the flag moulded onto the tens wheel covers the units wheel number, thus blanking the display.

Each time a dose is delivered, the motion of the canister carriage indexes the counter. As the carriage moves down, the escapement-type rocker is pivoted relative to the chassis to index the units wheel. A drive feature on the end of the units wheel rotates the geneva wheel through 60° once per revolution of the units wheel, with the geneva wheel incorporating lugs to stop it rotating when not driven by the units wheel. The geneva wheel is directly geared to the tens wheel which enables that wheel to be indexed. A lug inside the cover 10 prevents the tens wheel moving beyond the empty flag position. In this position, the drive from the geneva is disengaged, thus enabling the rest of the mechanism to continue operating as long as there is medication within the canister, although not to count the doses supplied in excess of 129 doses.

Figure 11:
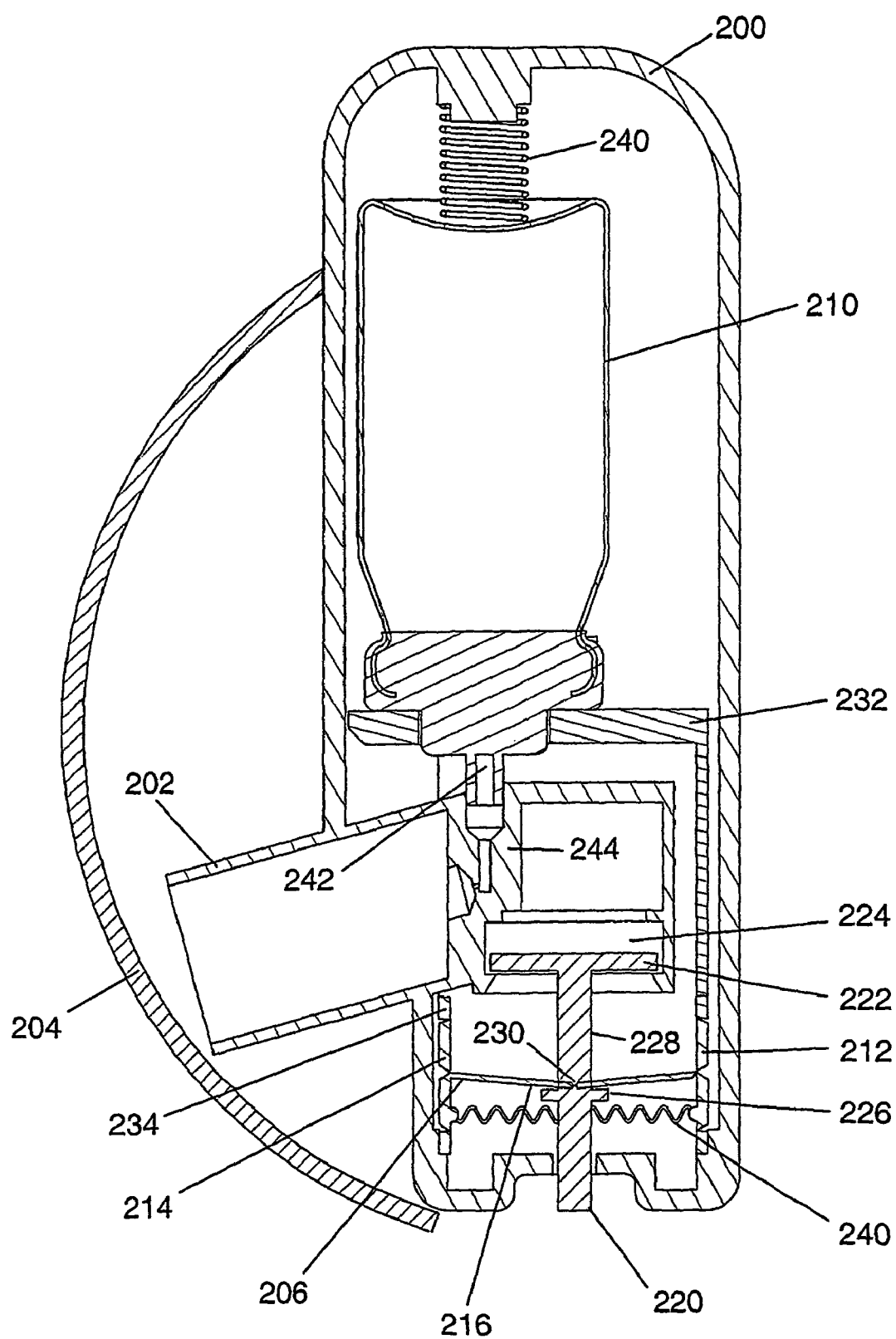
FIG. 11 illustrates a vertical section through an inhaler incorporating a fourth embodiment of the dose-actuation mechanism before firing.
Figure 12:
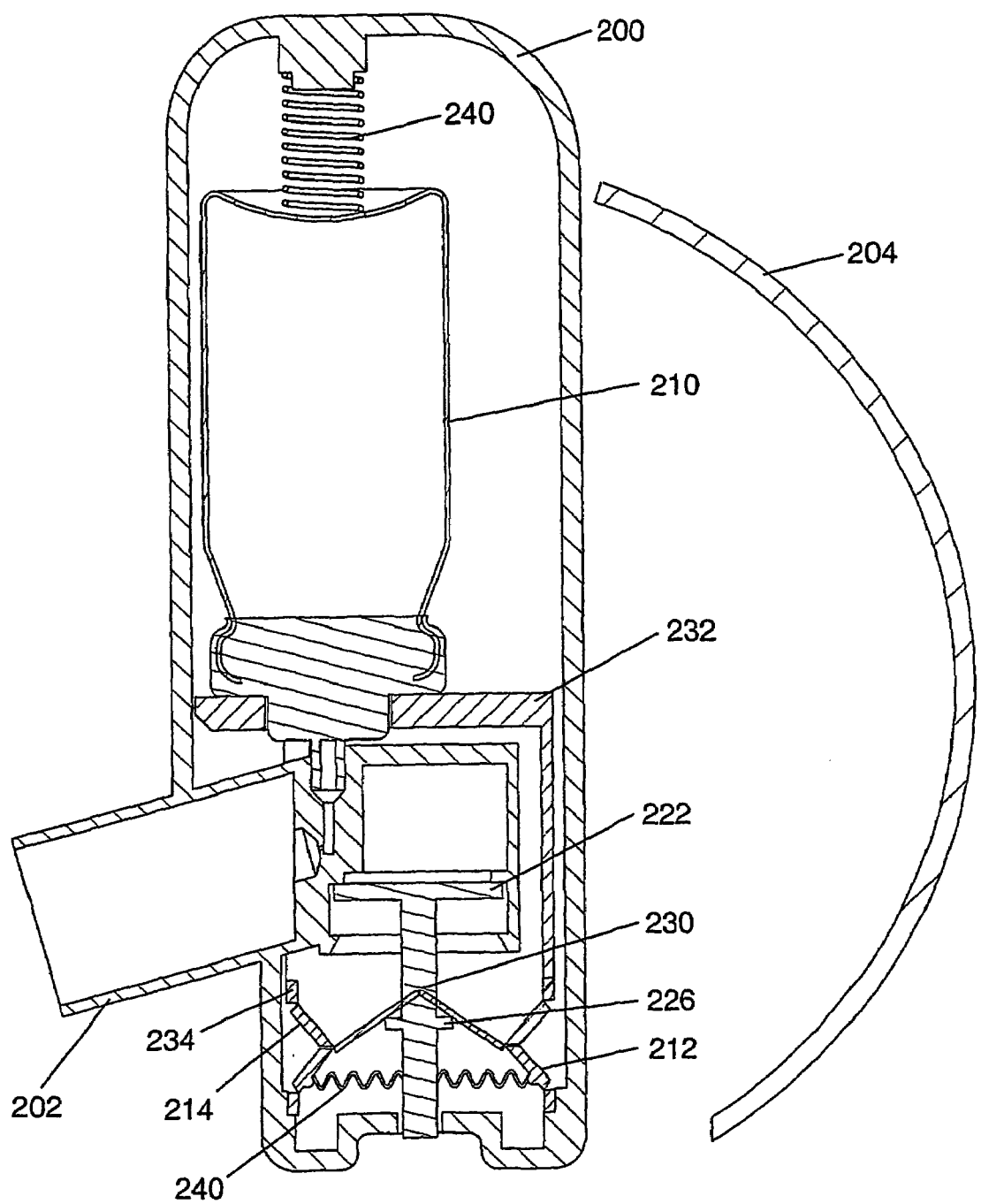
FIG. 12 corresponds to FIG. 11 but shows the mechanism after firing.
Figure 13:
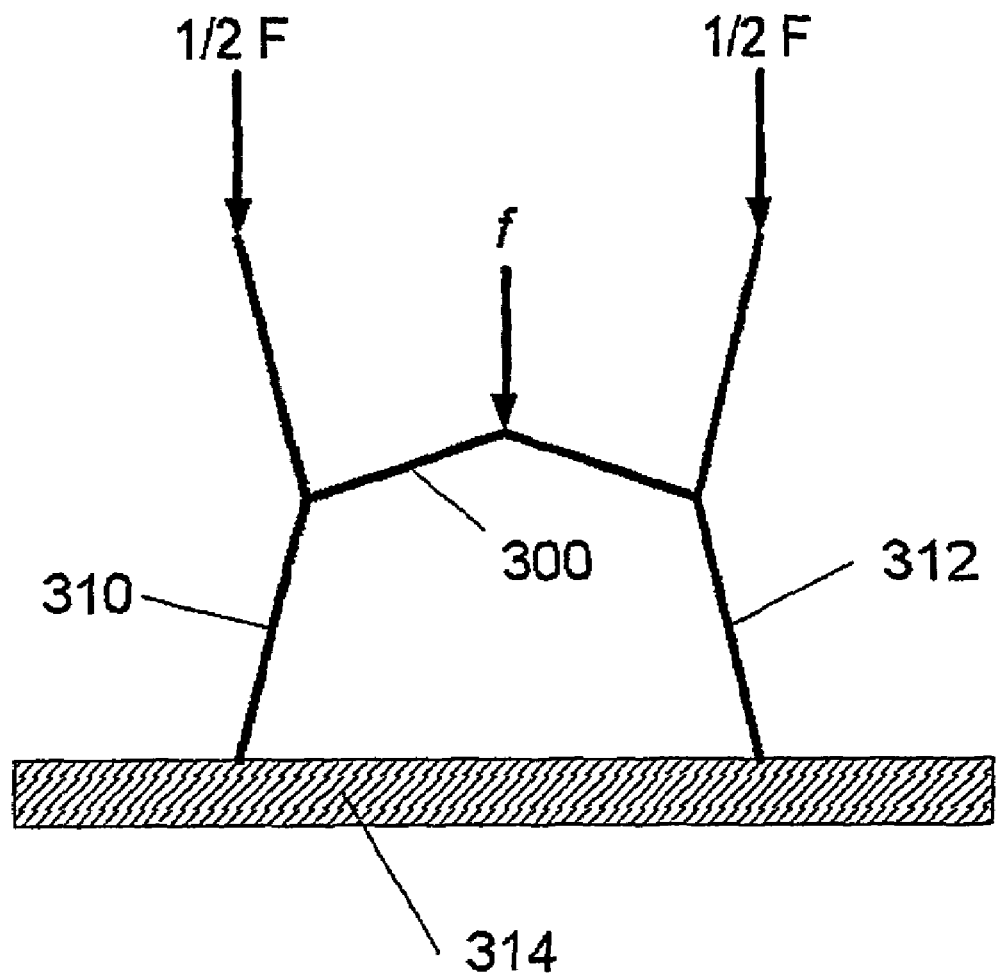
FIG. 13 is a schematic view used to explain operation of the fourth embodiment.

A further embodiment of the inhaler is shown in FIGS. 11 and 12. The inhaler again comprises body 200 with mouthpiece 202 and cover 204. In this embodiment, trigger mechanism 206 is positioned within the body 200 away from canister 210 and the mechanism 206 comprises first and second power links 212, 214 and a trigger link 216. As before, each link comprises two elements joined together at a hinging point and, in this particular embodiment, each end of the trigger link 216 is joined to a respective hinging point of the first or second power link. The trigger mechanism is shown schematically in FIG. 13, and comprises a trigger link 300, power links 310, 312 and fixed stage 314.

The base of the device, i.e. the end of the body closest to the mouthpiece, incorporates a manual override button 220 which is moulded in one piece with an air flap 222 contained within chamber 224 at an inner end of the mouthpiece. The air flap/manual override moulding is substantially T-shaped with a lip 226 extending around the circumference part way along a leg 228 of the T, and a hinge 230 of the trigger link 216 rests against this lip when the trigger link is in the stable over center position. The power links 212, 214 support hollow cylinder 232 the lower end of which 234 which adjoins both power links.

When primed, the trigger link is initially held in a stable over center position, with the two power links 212, 214 each supporting a force of around 25N, i.e. the large force associated with main spring 240. Each power link is straight and thus when a force is applied to the trigger link to move it under center, the power links move under center, so allowing the push rod to fall and release the stored energy within spring 240. Thus as the patient breathes in a force of around 0.2–0.4N is generated and the air flap 222 acts as a piston and lifts, i.e. moves towards, the canister 210 so pulling the trigger link 216 towards the canister and into an under center position. The same effect can be achieved by pushing on the manual override button. As the trigger link 216 moves under center, the power links 212, 214 fall further under center, as shown in FIG. 12, and move into a V shape so reducing their vertical height. The push rod 232 is released, and spring 240 is now free to expand and urge valve 242 against boss 244, so dispensing a dose. A biasing spring 240 connects the two power links and ensures that the straight links move when the trigger link moves under center.

Whilst two power links are shown, this number could be increased, for example by having a polar array of power links with a star-shaped trigger link. This trigger link would have one member attached to each power link in the array.

The multiple power links allow the large force required to actuate a canister to be shared between linkages and so reduce the loading on individual hinging points.

The trigger mechanisms discussed herein in their various embodiments allow reliable actuation of the device over at least 300 cycles, or doses, without failure of the components, and are such that manufacturing tolerances are not critical to the performance of the trigger mechanisms. It can readily be envisaged that such links could be used in other types of dosing devices where a small force acting on a trigger is required to release a much larger force.

The invention claimed is:

1. A dosing device comprising a dispenser for dispensing a dose material and a dose actuation mechanism comprising a first link and a second link, wherein the second link comprises a first element and a second element hinged together at a hinging point, and the first link comprises third and fourth elements hinged together at a second hinging point, with the second hinging point arranged to abut a stop so as to ensure that the first link is held in an over-center position when in a rest position prior to operation of the device, and a first end of the first link attached to the second link near the hinging point, whereby the second link is held in an under-center position by the first link and is moveable to further under-center in response to movement of the first link.

2. A dosing device according to claim 1, wherein a deflectable member is attached to the third element and is moveable in response to air flow, so as to cause the first link to move.

3. A dosing device according to claim 2, wherein the first link rests at an over center position prior to operation of the device, and the first link moves under center during operation of the device to trigger movement of the second link.

4. A dosing device according to claim 3, wherein the hinged elements are independently moveable about the respective hinging points.

5. A dosing device according to claim 4, wherein in the rest position, the third and fourth elements of the first link are disposed about the second hinging point to form a V-shape, with a force acting on the second hinging point to maintain the V-shaped link in an over center position.

6. A dosing device according to claim 1, wherein the dose actuation mechanism further comprises a third link comprising fifth and sixth elements joined at a third hinging point, one end of the second link connected near the third hinging point.

7. A dosing device according to claim 1, wherein the dose actuation mechanism further comprises a fourth link comprising seventh and eighth elements joined at a fourth hinging point, a second end of the first link connected to the fourth link near the fourth hinging point, such that the first link is interposed between the second and fourth links.

8. A dosing device according to claim 7, wherein a biasing means adjoins the second hinging point, the biasing means urging against the second hinging point so as to ensure that the second link responds to movement of the first link to transfer force along the mechanism.

9. A dosing device according to claim 8, wherein in the rest position the third and fourth elements form a substantially linear link, so that a small force is needed to actuate the first link.

10. A dosing device according to claim 9, wherein the first and second links, or first, second and third links are formed in a one-piece moulding made from plastics material, polypropylene or nylon.

11. A dosing device according to claim 1, wherein the first link rests at an over center position prior to operation of the device, and the first link moves under center during operation of the device to trigger movement of the second link.

12. A dosing device according to claim 1, wherein the hinged elements are independently moveable about the respective hinging points.

13. A dosing device according to claim 1, wherein in the rest position, the third and fourth elements of the first link are disposed about the second hinging point to form a V-shape, with a force acting on the second hinging point to maintain the V-shaped link in an over center position.

14. A dosing device according to claim 1, wherein the second link is arranged so that it is held in an under center position by the first link and is moveable to further under center in response to movement of the first link.

15. A dosing device according to claim 1, wherein the dose actuation mechanism further comprises a third link comprising fifth and sixth elements joined at a third hinging point, one end of the second link connected near the third hinging point.

16. A dosing device according to claim 1, wherein the dose actuation mechanism further comprises a fourth link comprising seventh and eighth elements joined at a fourth hinging point, a second end of the first link connected to the fourth link near the fourth hinging point, such that the first link is interposed between the second and fourth links.

17. A dosing device according to claim 1, wherein a biasing means adjoins the second hinging point, the biasing means urging against the second hinging point so as to ensure that the second link responds to movement of the first link to transfer force along the mechanism.

18. A dosing device according to claim 1, wherein in the rest position the third and fourth elements form a substantially linear link, so that a small force is needed to actuate the first link.

19. A dosing device according to claim 1, wherein the first and second links, or first, second and third links are formed in a one-piece moulding made from plastics material, polypropylene or nylon.

20. A dose actuation mechanism for use in a dosing device, comprising a first link and a second link, wherein the second link comprises a first element and a second element hinged together at a hinging point, and the first link comprises third and fourth elements hinged together at a second hinging point, with the second hinging point arranged to abut a stop so as to ensure that the first link is held in an over-center position when in a rest position prior to operation of the device, and a first end of the first link is attached to the second link near the hinging point whereby the second link is held in an under-center position by the first link and is moveable to further under-center in response to movement of the first link.

21. A dose actuation mechanism according to claim 20, wherein the first link comprises third and fourth elements connected by a thin web so as to provide a further hinging point within the first link.

22. A dose actuation mechanism according to claim 20, wherein the third element has integral strengthening ribs.

23. A dose actuation mechanism according to claim 22, wherein the second element of the second link is hingeably connected to a third link with a fourth and fifth element, the fourth and fifth elements connected to each other by two separate webs to form a yet further hinging point.

24. A dose actuation mechanism according to claim 21, wherein the second element of the second link is hingeably connected to a third link with a fourth and fifth element, the fourth and fifth elements connected to each other by two separate webs to form a yet further hinging point.

25. A dose actuation mechanism according to claim 24 when made as a one-piece moulding from plastics material.

* * * * *